US009949669B2

(12) United States Patent
DiSilvestro et al.

(10) Patent No.: US 9,949,669 B2
(45) Date of Patent: *Apr. 24, 2018

(54) SYSTEM AND METHOD FOR DETERMINING PATIENT FOLLOW-UP SUBSEQUENT TO AN ORTHOPEDIC PROCEDURE

(71) Applicant: DEPUY SYNTHES PRODUCTS, INC., Raynham, MA (US)

(72) Inventors: Mark R. DiSilvestro, Columbia City, IN (US); Terry L. Dietz, Columbia City, IN (US); Robert S. Hastings, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 326 days.

This patent is subject to a terminal disclaimer.

(21) Appl. No.: 14/736,802

(22) Filed: Jun. 11, 2015

(65) Prior Publication Data

US 2015/0272477 A1 Oct. 1, 2015

Related U.S. Application Data

(60) Continuation of application No. 14/223,393, filed on Mar. 24, 2014, now Pat. No. 9,055,918, which is a
(Continued)

(51) Int. Cl.
*A61B 5/107* (2006.01)
*A61B 5/00* (2006.01)
(Continued)

(52) U.S. Cl.
CPC .......... *A61B 5/1071* (2013.01); *A61B 5/0002* (2013.01); *A61B 5/0031* (2013.01); *A61B 5/076* (2013.01); *A61B 5/1118* (2013.01); *A61B 5/4528* (2013.01); *A61B 5/4851* (2013.01); *A61F 2/30* (2013.01); *A61B 5/1076* (2013.01); *A61F 2/38* (2013.01);
(Continued)

(58) Field of Classification Search
CPC ...... A61B 5/4851; A61B 5/1118; A61B 5/112
See application file for complete search history.

(56) References Cited

U.S. PATENT DOCUMENTS 5,042,504 A * 8/1991 Huberti ................ A61B 5/1036
600/592
5,197,488 A 3/1993 Kovacevic
(Continued)

FOREIGN PATENT DOCUMENTS

WO 9938052 A1 7/1999

OTHER PUBLICATIONS

European Search Report for European Application No. EP05257905.9-2201, dated Apr. 3, 2006, 6 pages.
(Continued)

*Primary Examiner* — Michael C Stout
(74) *Attorney, Agent, or Firm* — Barnes & Thornburg LLP

(57) ABSTRACT

A method of determining patient follow-up subsequent to an orthopaedic procedure includes determining the number of cycles of use of an orthopaedic joint of the patient. If a predetermined threshold is exceeded, communication with an orthopaedic care provider is initiated. A patient monitoring system is also disclosed.

14 Claims, 4 Drawing Sheets

Related U.S. Application Data division of application No. 13/300,535, filed on Nov. 18, 2011, now Pat. No. 8,702,799, which is a continuation of application No. 11/024,888, filed on Dec. 29, 2004, now abandoned.

(51) Int. Cl.

| | | |
|---|---|---|
| *A61B 5/07* | (2006.01) | |
| *A61B 5/11* | (2006.01) | |
| *A61F 2/30* | (2006.01) | |
| *A61F 2/38* | (2006.01) | |
| *A61F 2/48* | (2006.01) | |
| *G06F 19/00* | (2018.01) | |

(52) U.S. Cl.
CPC ............... *A61F 2002/3067* (2013.01); *A61F 2002/30953* (2013.01); *A61F 2002/488* (2013.01); *A61F 2250/0002* (2013.01); *G06F 19/3418* (2013.01); *G06F 19/3481* (2013.01)

(56) References Cited

U.S. PATENT DOCUMENTS

| | | | |
|---|---|---|---|
| 6,075,755 A | 6/2000 | Zarchan | |
| 6,184,797 B1 | 2/2001 | Stark et al. | |
| 6,245,109 B1 * | 6/2001 | Mendes | A61B 5/06 |
| | | | 623/18.11 |
| 6,442,527 B1 | 8/2002 | Worthington | |
| 6,447,448 B1 * | 9/2002 | Ishikawa | A61B 5/0031 |
| | | | 128/899 |
| 6,573,706 B2 * | 6/2003 | Mendes | A61B 5/06 |
| | | | 324/207.17 |
| 6,705,991 B2 | 3/2004 | Bardy | |
| 6,821,299 B2 * | 11/2004 | Kirking | A61B 5/4528 |
| | | | 600/587 |
| 7,347,874 B2 | 3/2008 | DiSilvestro | |
| 9,055,918 B2 | 6/2015 | DiSilvestro et al. | |
| 2002/0035493 A1 | 3/2002 | Mozayeny et al. | |
| 2002/0087116 A1 | 7/2002 | Hartlaub | |
| 2002/0137991 A1 | 9/2002 | Scarantino | |
| 2004/0019382 A1 | 1/2004 | Amirouche et al. | |
| 2004/0034355 A1 * | 2/2004 | Govari | A61B 17/1707 |
| | | | 606/98 |
| 2005/0010299 A1 | 1/2005 | DiSilvestro | |
| 2005/0010301 A1 | 1/2005 | DiSilvestro et al. | |
| 2006/0047283 A1 * | 3/2006 | Evans, III | A61B 5/1076 |
| | | | 606/102 |
| 2006/0052782 A1 * | 3/2006 | Morgan | A61B 90/06 |
| | | | 606/60 |

OTHER PUBLICATIONS

"Total Knee Replacement: Caring for Yourself at Home." California Pacific Medical Center. 2002, 6 pages <www.cpmc.org/learning>.

Basu, D. "Fatigue behaviour of fine-grained alumina hip-joint heads under normal walking conditions." Sadhana vol. 28, Parts 3 and 4, Jun./Aug. 2003. pp. 589-600.

* cited by examiner

# SYSTEM AND METHOD FOR DETERMINING PATIENT FOLLOW-UP SUBSEQUENT TO AN ORTHOPEDIC PROCEDURE

CROSS-REFERENCE TO RELATED U.S. PATENT APPLICATION

This application is a continuation application of U.S. patent application Ser. No. 14/223,393, filed Mar. 24, 2014, which is a divisional application of U.S. patent application Ser. No. 13/300,535, now U.S. Pat. No. 8,702,799, which was filed on Nov. 18, 2011 and was a continuation application of U.S. application Ser. No. 11/024,888 entitled "SYSTEM AND METHOD FOR DETERMINING PATIENT FOLLOW-UP SUBSEQUENT TO AN ORTHOPAEDIC PROCEDURE" by Mark D. DiSilvestro et al., which was filed on Dec. 29, 2004, the entirety of which is hereby incorporated by reference.

FIELD OF DISCLOSURE

The present disclosure relates generally to systems and methods for use in conjunction with orthopaedic procedures.

BACKGROUND

Currently, patient follow-up subsequent to an orthopaedic procedure is a function of the time that has elapsed since the procedure. Indeed, follow-up meetings with the orthopaedic care provider (e.g., the surgeon) are typically scheduled for dates in the future which reflect the passage of a given amount of time since the procedure.

SUMMARY

According to one aspect, a system for monitoring a patient's use of an orthopaedic joint which includes first and second joint prosthesis components includes an implantable sensor, a processor, and a memory device. The implantable sensor, when implanted in a patient, can be used to monitor the number of cycles of use of the orthopaedic joint. The processor in communication with the sensor. The memory device is electrically coupled to the processor and has stored therein a plurality of instructions which, when executed by the processor, cause the processor to (i) monitor output from the sensor to determine the number of cycles of use of the orthopaedic joint and (ii) to generate a message to the patient indicative of a need to initiate communication with an orthopaedic care provider if the number of cycles of use of the orthopaedic joint exceeds a predetermine threshold value. In some embodiments, the implantable sensor may be embodied as a permanent magnet embedded in the first joint prosthesis component and a Hall effect switch embedded in the second joint prosthesis component. The system may further comprising electronics associated with the permanent magnet and the Hall effect switch that are adapted to determine the number of occasions in which the first and second joint prosthesis component are in a predetermined position relative to one another.

In some embodiments, the processor and memory device are embedded in one of the first and second joint prostheses. Alternatively, the processor and memory device may be located in a data interpretation device separate from the orthopaedic joint. In such embodiments, the electronics may include a transmitter to transmit data indicative of the number of occasions in which the first and second joint prosthesis component are in the predetermined position relative to one another to the data interpretation device. Additionally or alternatively, the electronics may be configured to determine the number of occasions in which a predetermined angle of flexion is attained by the orthopaedic joint. For example, the predetermined angle of flexion is indicative of a step having been taken by the patient. In some embodiments, the message may be at least one of an audible message and a visual message.

According to another aspect, a system for determining patient follow-up subsequent to an orthopaedic procedure may include an orthopaedic prosthesis and a computing device. The orthopaedic prosthesis may include a femoral component having a signal source embedded therein and a tibial component having an electrical circuit embedded therein. The electrical circuit may include a sensor to generate a data signal in response to the signal source. Additionally, the electrical circuit may be configured to (i) determine the number of occasions in which the femoral component and the tibial component are in a predetermined position relative to one another as a function of the data signal, (ii) calculate a cycle count indicative of a cumulative number of cycles of use of the orthopaedic prosthesis, and (iii) transmit the cycle count. The computing device may be configured to receive the data signal and generate a message indicating a need to initiate communication with an orthopaedic care provider in response to the cycle count exceeding a reference threshold value.

In some embodiments, the signal source may be embodied as a permanent magnet and the sensor may be embodied as a Hall effect switch. Additionally or alternatively, the computing device may include a display. In such embodiments, the message comprises a visual message displayed on the display of the computing device. In some embodiments, the computing device may be further configured to initiate a communication with the orthopaedic care provider in response to the cycle count exceeding the reference threshold value. For example, the computing device may be configured to generate an e-mail to the orthopaedic care provider. Additionally or alternatively, the computing device may be configured to initiate a telephone call to an office of the orthopaedic care provider.

In some embodiments, the computing device may include communication circuitry, a display, a processor, and a memory. The memory may have stored therein a plurality of instructions that, in response to the processor, cause the processor to generate a visual message to the patient on the display that indicates a need to initiate communication with the orthopaedic care provider in response to the cycle count exceeding the reference threshold value and initiate a communication with the orthopaedic care provider in response to the cycle count exceeding the reference threshold value.

According to a further aspect, a method for determining patient follow-up subsequent to an orthopedic procedure may include generating a data signal with a Hall effect switch embedded in a first joint component of an implanted joint prosthesis in response to a permanent magnet embedded in a second joint component of the implanted joint prosthesis. the method may also include generating a cycle count indicative of the number of occasions in which the first and second joint components are in a pre-determined position relative to one another. Additionally, the method may include transmitting the cycle count to a computing device external to the patient, comparing the cycle count to a reference threshold, and initiating communication with an orthopaedic care provider in response the cycle count having a predetermined relationship with the reference threshold.

In some embodiments, the method may include generating an e-mail to the orthopaedic care provider and/or initiating a telephone call to an office of the orthopaedic care provider. Additionally, in some embodiments, the method may include generating a message on the computing device indicating a need to initiate communication with the orthopaedic care provider in response to the cycle count having the predetermined relationship with the reference threshold value. The method may also include electronically querying the implanted joint prosthesis with the computing device to obtain the cycle count. Additionally or alternatively, the method may include transmitting the cycle count comprises transmitting the cycle count to the computing device in response to a query received from the computing device.

BRIEF DESCRIPTION OF THE DRAWINGS

The detailed description particularly refers to the accompanying figures in which.

DETAILED DESCRIPTION OF THE DRAWINGS

The present disclosure relates to a method for determining patient follow-up after an orthopaedic procedure, such as a joint replacement procedure, based on the actual use of the patient's joint. As will be described herein in greater detail, the number of cycles of use of the patient's joint may be determined, for example, by (i) determining number of steps taken by the patient, (ii) determining the activity level of the patient, (iii) determining the number of times a predetermined joint flexion angle is achieved, or (iv) determining the number of loading cycles of the joint. Determination of these parameters may be achieved in a number of different manners. When it is determined that the patient has achieved a level of use in which follow-up is desired, a communication with the orthopaedic care provider (e.g., a surgeon, hospital, nurse, primary care provider, or other individual involved in the care of the patient) is initiated by notifying the patient and/or the orthopaedic care provider. As will be described herein in greater detail, such communication may be achieved in a variety of different manners.

Figure 1:
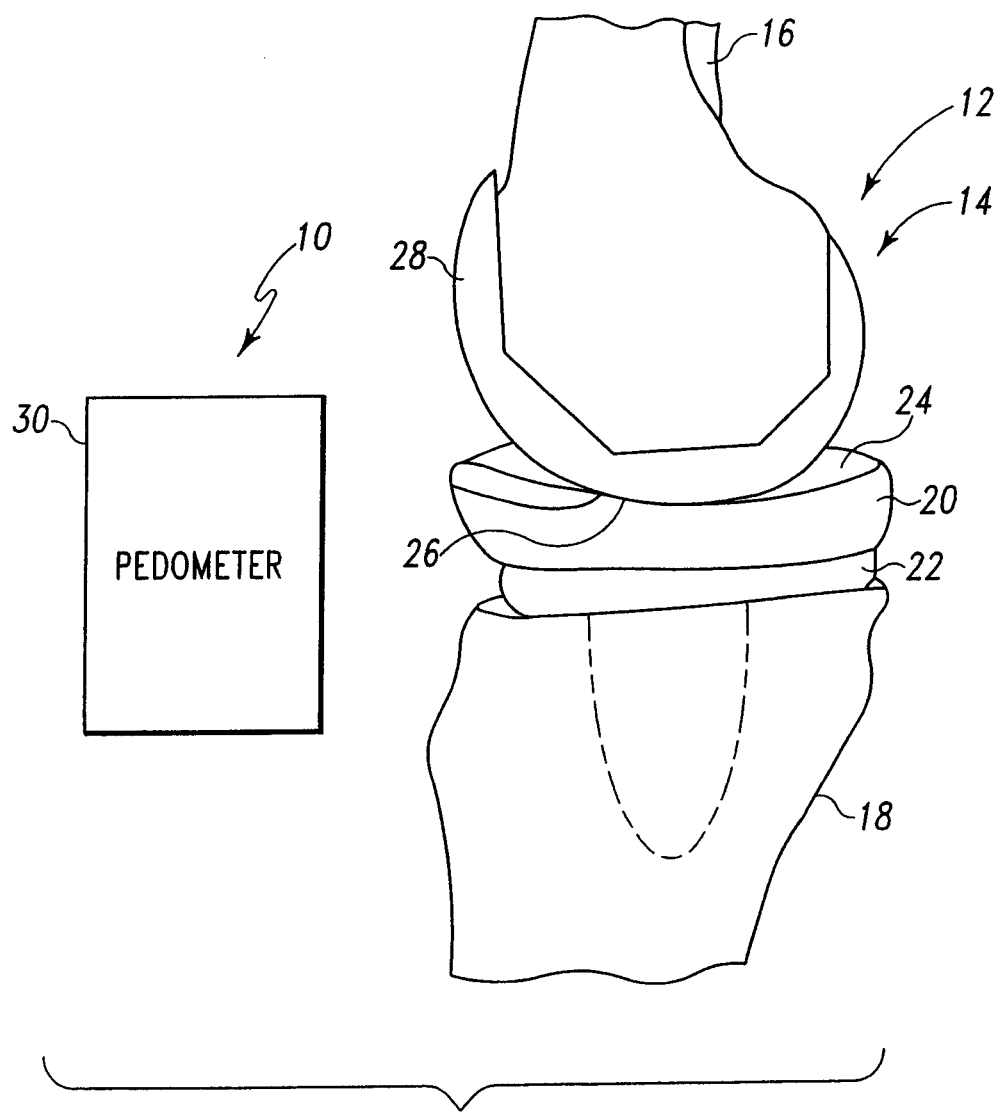
FIG. 1 is a diagrammatic view showing a joint use measurement device in the form of a pedometer being utilized to determine the cycles of use of a knee endoprosthesis system.

Referring now to FIG. 1, there is shown one implementation of the concepts of the present disclosure. In this case, a joint use measurement device 10 is utilized to determine the number of cycles of use of a prosthetic orthopaedic joint 12. In the exemplary arrangement of FIG. 1, the orthopaedic joint 12 is exemplary embodied as a knee endoprosthesis system 14 for use in a total knee replacement procedure. The knee endoprosthesis system 14 is implanted on the distal end of the femur 16 and the proximal end of the tibia 18. The endoprosthesis system 10 includes a tibial bearing 20 that is positioned on the proximal tibial component 22. The proximal tibial component 22 is affixed to the proximal end of the tibia 18. The tibial bearing 20 has a contoured proximal surface 24, against which the condyles 26 of the distal femoral component 28 bear. The distal femoral component 28 is affixed to the distal end of the femur 16. Articulation of the joint is at the interface of the proximal surface 24 of the tibial bearing 20 and the condyles 26 of the distal femoral component 28.

The actual use of the knee endoprosthesis system 14 may be characterized as cycles of use of the system. The cycles of use of the system 14 may be measured in a variety of methods such as, for example, (i) by determining number of steps taken by the patient, (ii) by determining the activity level of the patient, (iii) by determining the number of times a predetermined joint flexion angle is achieved by the system 14, or (iv) by determining the number of loading cycles of the system 14.

In the exemplary embodiment shown in FIG. 1, the joint use measurement device 10 is embodied as a pedometer 30. The pedometer 30 is worn by the patient subsequent to the patient's orthopaedic procedure to determine the number of steps taken by the patient. When the output from the pedometer 30 indicates that the patient has taken a predetermined number of steps since the patient's orthopaedic procedure (or since the patient's previous meeting with the surgeon), a communication with the orthopaedic surgeon may be initiated. For example, the patient may make an appointment with the surgeon's office via telephone, electronic mail or other web-based communication, conventional mail, etcetera.

Figure 2:
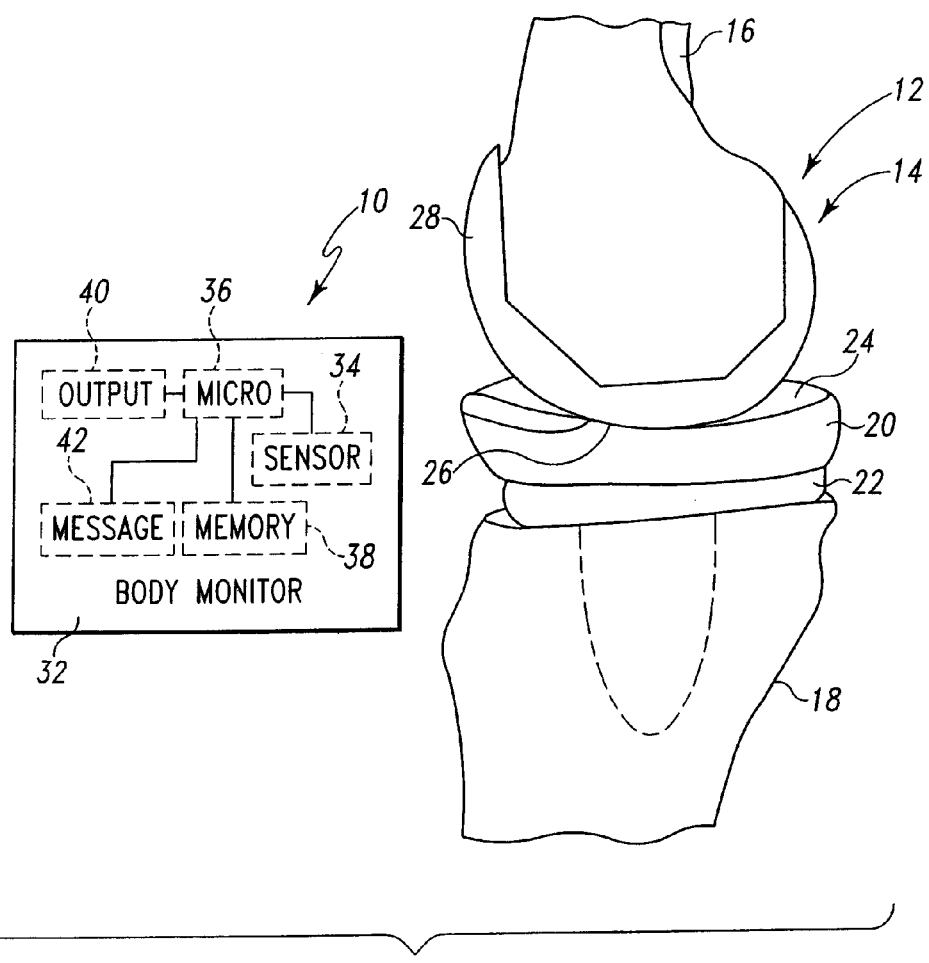
FIG. 2 is a diagrammatic view showing a joint use measurement device in the form of a electronic body monitor being utilized to determine the cycles of use of a knee endoprosthesis system.

Referring now to FIG. 2, there is shown an arrangement similar to FIG. 1, but showing the joint use measurement device 10 embodied as an electronic body monitor 32. The electronic body monitor 32 is configured to be worn externally of the patient's body such as, for example, on an armband. Like the pedometer 30 of FIG. 1, the electronic body monitor 32 may be used to determine the number of steps taken by the patient over a given period of time (e.g., since the patient's procedure or since the patient's previous post-surgical meeting with the surgeon). The electronic body monitor 32 may also execute algorithms for determining and tracking the activity level of the patient. In this way, follow-up may be initiated as a function of steps taken by the patient, activity level of the patient, or both.

As shown in FIG. 2, the electronic body monitor 32 includes a sensor 34 that is configured to sense parameters associated with cycles of use of the knee endoprosthesis system 14. The sensor 34 may be embodied as a single sensor or as an array of sensors. In one exemplary embodiment, the sensor 34 is embodied as a two-axis accelerometer the output from which may be used to determine the number of steps taken by the patient. The electronic body monitor 32 also includes a processor 36 electrically coupled to the sensor 34, a memory device 38, and a data output port 40. The processor 36 is electrically coupled to the data output port 40 and the memory device 38. The electronic body monitor 32 may also include other devices useful in a computing device such as drivers, registers, buffers, digital signal processors, and the like. Illustratively, the electronic body monitor 32 may be embodied, with or without modification thereto, as any one of the numerous body monitors commercially available from BodyMedia, Incorporated of Pittsburgh, Pa. One such BodyMedia device is commercially sold under the name SenseWare PRO.

The processor 36 and memory device 38 cooperate to determine when follow-up subsequent to an orthopaedic procedure is warranted based on cycles of use of the knee endoprosthesis system 14. In particular, the memory device 38 has stored therein a plurality of instructions in the form of a software routine which performs such a function. The memory device 38 may be Random Access Memory (hereinafter sometimes RAM), Read Only Memory (hereinafter sometimes ROM), flash or erasable memory such as Erasable Programmable ROM (hereinafter sometimes EPROM) and Electrically Erasable Programmable ROM (hereinafter sometimes EEPROM), and/or other memory devices. Due to the adaptable nature of programming languages, there are many embodiments of a software routine stored in the memory device 38 for performing such a function.

The electronic body monitor 32 also includes a message generating device 42. The message generating device 42 is operable to generate visual and/or audible messages for presentation to the patient. For example, when the electronic body monitor 32 determines that the patient has exceeded a predetermined threshold relating to the number of steps taken by the patient (or activity level) since the patient's procedure (or last meeting with the surgeon), an audible and/or visual alert may be generated by the message generating device 42. The message generating device 42 may be embodied as any type of such device including, for example, an LCD or LED display and/or a tone/sound generator.

Figure 3:
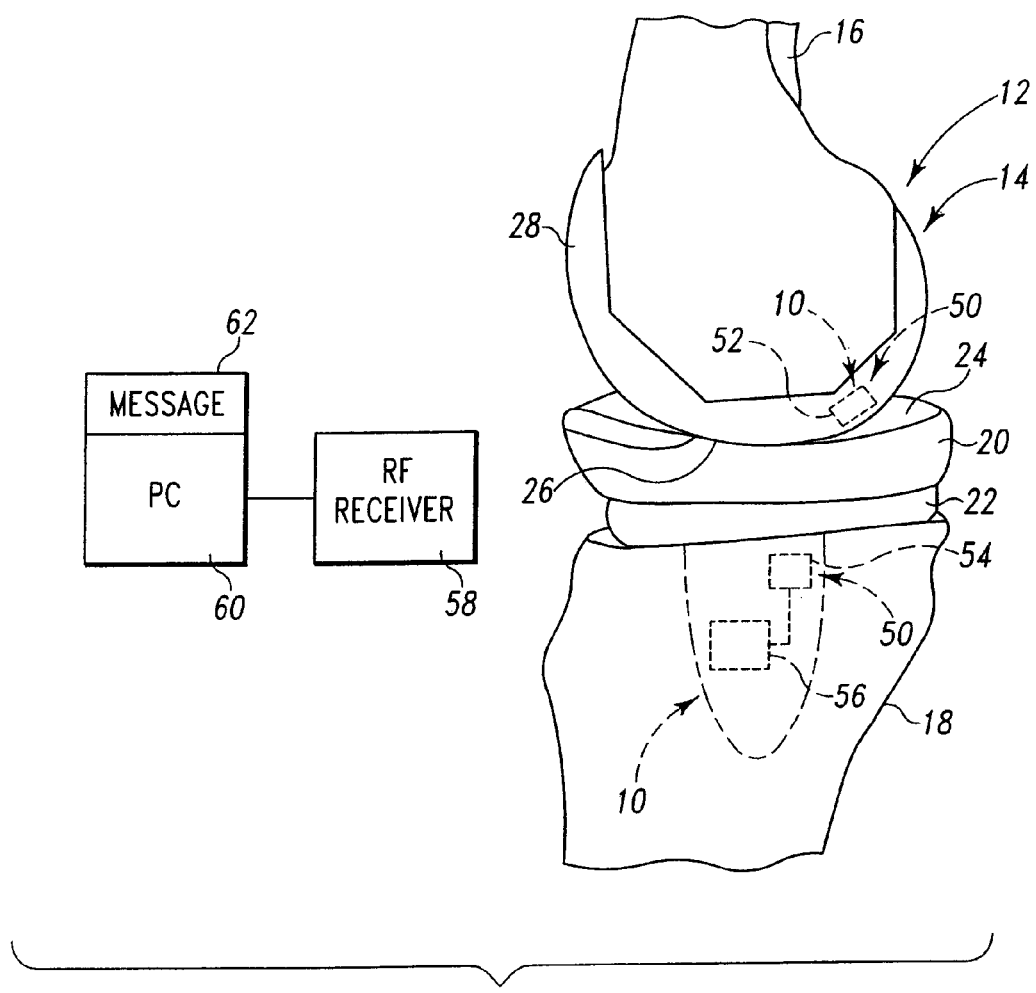
FIG. 3 is a diagrammatic view showing a joint use measurement device in the form of an implantable joint cycle counter being utilized to determine the cycles of use of a knee endoprosthesis system.

Referring now to FIG. 3, the joint use measurement device 10 includes an implanted sensor 50. The sensor 50 may be embodied as a single sensor or as an array of sensors. In the exemplary embodiment of FIG. 3, the implanted sensor 50 includes a signal source 52, such as a permanent magnet, that is embedded in the distal femoral component 28, and a sensor 54, such as a Hall effect switch, embedded in the proximal tibial component 22. The associated electronics 56 are also secured to the proximal tibial component 22. The electronics 56 include, amongst other things, a processor, memory device, power source, modulator, a transmitter, and antenna to facilitate the maintenance of a running count of the number of times the knee endoprosthesis system 14 cycles, along with the ability to transmit such a count from within the patient's body. In other words, the joint use measurement device 10 illustrated in FIG. 3 utilizes an implanted sensor to determine the number of occasions in which the components of the knee endoprosthesis system 14 are in a predetermined relative position with one another (e.g., the number of occasions in which a predetermined flexion angle is attained), thereby determining cycles of use of the system 14.

The stored count information can be transmitted to a device external to the patient's body by use of the transmitter and antenna of the associated electronics 56. As shown schematically in FIG. 3, an external receiver 58 and data interpretation device 60 may be used to retrieve information from the implanted electronics 56. The external receiver 58 may be embodied as a radio-frequency antenna that is operable to receive the signal from the internal antenna of the implanted electronics 56. The data interpretation device 60 is electrically coupled to the receiver 58, and may be embodied as a standard computer (e.g., PC) programmed to demodulate the radio-frequency signal received from the internal transmitter and the internal antenna of the implanted electronics 56. The data interpretation device 60 may also be embodied as a hand-held personal computer, a personal desk assistant, a laptop computer, or any custom-designed data acquisition device. The data interpretation device 60 may be programmed to perform calculations necessary to convert the received and demodulated signal into the number of cycles recorded by the counter.

One such implantable system, along with the associated external components, is disclosed in U.S. patent application Ser. No. 10/887,766, entitled "In Vivo Joint Implant Cycle Counter" which is assigned to the assignee of the present application, and which is hereby incorporated by reference.

The data interpretation device 60 may have integrated therein, or be coupled to, a message generating device 62. The message generating device 62 is operable to generate visual and/or audible messages for presentation to the patient. For example, when it is determined from the output of the implanted electronics 56 that the number of occasions in which the knee endoprosthesis system 14 has attained a predetermined flexion angle has exceeded a predetermined threshold, an audible and/or visual alert may be generated by the message generating device 62. The message generating device 62 may be embodied as any type of such device including, for example, a PC display monitor, an LCD or LED display, and/or a tone/sound generator.

In lieu of the arrangement of FIG. 3 which includes a magnet and Hall effect switch, other implanted sensor arrangements are also contemplated. For example, a load sensor may be implanted into the knee endoprosthesis system 14. In such a system, the cycles of use of the system 14 could be determined by counting loading cycles of the system. Such a count could be stored, transmitted, and received in a similar manner to as described above in regard to the arrangement of FIG. 3.

In another example, the cycles of use of the patient's joint may be determined by measuring the wear of certain components of the knee endoprosthesis system 14. For instance, a sensor arrangement may be utilized in which the joint space between the femoral component 28 and the tibial component 22 is measured/monitored. It should be appreciated that such a distance may shorten (i.e., reduce) over cycles of the knee endoprosthesis system as a result of wear of the tibial bearing 20. As such, the cycles of use of the system 14 could be determined by measuring and tracking the joint space between the femoral component 28 and the tibial component 22. Such data could be stored, transmitted, and received in a similar manner to as described above in regard to the arrangement of FIG. 3. One such implantable system, along with the associated external components, is disclosed in U.S. patent application Ser. No. 10/888,243, entitled "System and Method for Determining Patient Follow-Up Subsequent to an Orthopaedic Procedure" which is assigned to the assignee of the present application, and which is hereby incorporated by reference.

Figure 4:
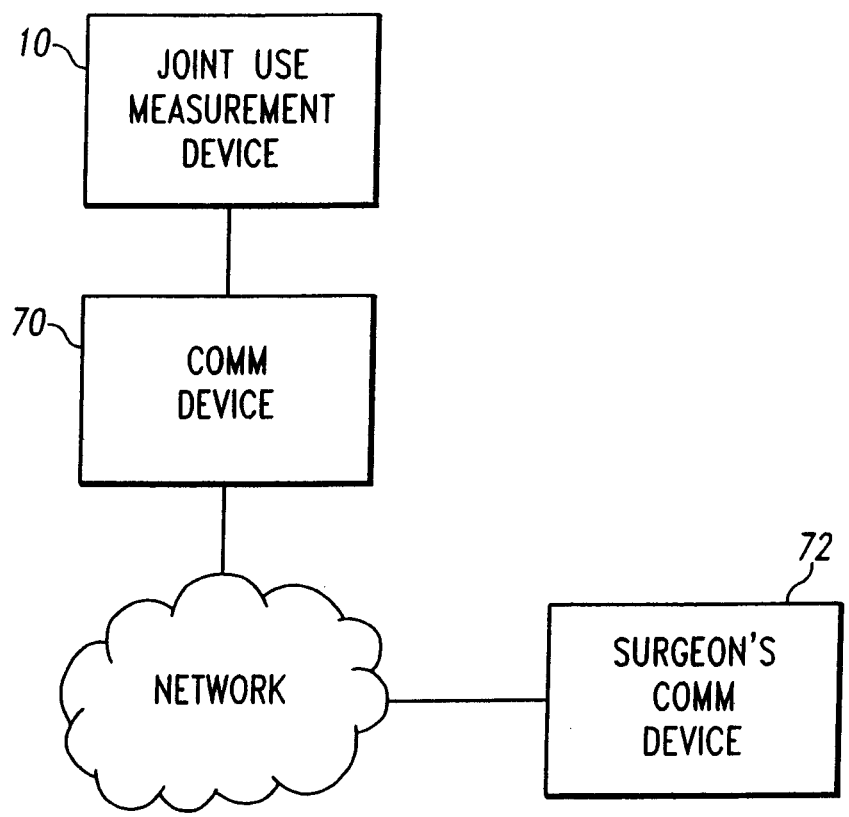
FIG. 4 is a diagrammatic view showing a joint use measurement device in communication with a communication device.

Referring now to FIG. 4, there is shown the joint use measurement device 10 being used in conjunction with a communications device 70. The communications device 70 may be embodied as hardware and software that is integrated into a personal computer, wireless (e.g., cellular) telephone, PDA, or home automation system. Alternatively, the communications device 70 may be a discreet hardware/software assembly electrically coupled to a personal computer, wireless (e.g., cellular) telephone, PDA, or home automation system. In either case, the communications device 70 includes devices useful in a computing device such as microprocessor(s), memory devices, drivers, registers, buffers, digital signal processors, and the like The communications device 70 may be operated to query the joint use measurement device 10 and then commence an automated, device-initiated communication with the orthopaedic care provider (e.g., the surgeon's office) if a follow-up visit is warranted based on the number of cycles of use of the knee endoprosthesis system 14. For example, the communications device 70 may initiate a telephone call, electronic mail communication, or other web-based communication with an electronic device or system 72 operated by the surgeon's office.

It should be appreciated that the communications device 70 may be configured to accommodate any one or more of the different exemplary embodiments of the joint use measurement device 10. For example, in the case of the electronic body monitor 32 of FIG. 2, the communications device 70 may be configured to communicate with the body monitor 32 via its data output port 40. Such a communication may be wired or wireless depending on the configuration of the port 40. It is contemplated to integrate the communications device 70 into the electronic body monitor 32.

Similarly, the communications device 70 may be configured to communicate with data interpretation device 60 of the arrangement of FIG. 3 via either a wired or wireless communication link. It should be appreciated that the communications device 70 may be integrated into the data interpretation device 60 (i.e., a single device, such as a PC, may be equipped with the necessary hardware and software to perform both the functions of the data interpretation device 60 and the functions of the communications device 70).

In the case of when the joint use measurement device 10 is embodied as a mechanical device (i.e., non-electrical) such as, for example, certain types of pedometers, data from the mechanical device may be input into the communications device 70. In such a case, the communications device 70 may be configured to process such manually entered data, and then, if appropriate, initiate communication with the surgeon in any one or more of the manners described above.

Although the concepts of the present disclosure have herein been described in regard to a knee prosthesis, it should be appreciated that the concepts described herein could also be applied to other joint endoprosthesis such as endoprosthesis systems for use in the hip, shoulder, wrist, elbow, ankle, along with endoprosthesis systems for use with the digits of the extremities. It should be understood that other configurations of a joint use measurement device (including its sensors) may be utilized to accommodate a given application in a desired joint location.

Moreover, although the concepts of the present disclosure have herein been exemplary described in regard to an endoprosthesis for use in a total joint replacement, it should be appreciated that the concepts described herein could also be applied to other arrangements. For example, the concepts of the present disclosure could be applied subsequent to a procedure in which the resultant joint includes one or more natural components. Moreover, the concepts of the present disclosure could be applied subsequent to an orthopaedic procedure at anatomical locations other than a joint.

While the disclosure is susceptible to various modifications and alternative forms, specific exemplary embodiments thereof have been shown by way of example in the drawings and has herein be described in detail. It should be understood, however, that there is no intent to limit the disclosure to the particular forms disclosed, but on the contrary, the intention is to cover all modifications, equivalents, and alternatives falling within the spirit and scope of the disclosure.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. A system for monitoring a patient's use of an orthopaedic joint which includes first and second joint prosthesis components, comprising:
    an implantable sensor which, when implanted in a patient, can be used to monitor the number of cycles of use of the orthopaedic joint,
    a processor in communication with the sensor, and
    a memory device electrically coupled to the processor, the memory device having stored therein a plurality of instructions which, when executed by the processor, cause the processor to (i) monitor output from the sensor to determine the number of cycles of use of the orthopaedic joint, and (ii) to generate a message to the patient indicative of a need to initiate communication with an orthopaedic care provider if the number of cycles of use of the orthopaedic joint exceeds a predetermine threshold value,
    wherein the implantable sensor comprises a permanent magnet embedded in the first joint prosthesis component and a Hall effect switch embedded in the second joint prosthesis component, the system further comprising electronics associated with the permanent magnet and the Hall effect switch that are adapted to determine the number of occasions in which the first and second joint prosthesis component are in a predetermined position relative to one another.

2. The system of claim 1, wherein the processor and the memory device are embedded in one of the first and second joint prostheses.

3. The system of claim 1, wherein the processor and the memory device are located in a data interpretation device separate from the orthopaedic joint.

4. The system of claim 3, wherein the electronics includes a transmitter to transmit data indicative of the number of occasions in which the first and second joint prosthesis component are in the predetermined position relative to one another to the data interpretation device.

5. The system of claim 1, wherein the electronics are configured to determine the number of occasions in which a predetermined angle of flexion is attained by the orthopaedic joint.

6. The system of claim 5, wherein the predetermined angle of flexion is indicative of a step having been taken by the patient.

7. The system of claim 1, wherein the message is at least one of an audible message and a visual message.

8. A system for determining patient follow-up subsequent to an orthopaedic procedure, the system comprising:
    an orthopaedic prosthesis comprising:
        a femoral component having a signal source embedded therein;
        a tibial component having an electrical circuit embedded therein, the electrical circuit comprising a sensor to generate a data signal in response to the signal source, the electrical circuit configured to (i) determine the number of occasions in which the femoral component and the tibial component are in a predetermined position relative to one another as a function of the data signal, (ii) calculate a cycle count indicative of a cumulative number of cycles of use of the orthopaedic prosthesis, and (iii) transmit the cycle count; and a computing device configured to receive the data signal and generate a message indicating a need to initiate communication with an orthopaedic care provider in response to the cycle count exceeding a reference threshold value.

9. The system of claim 8, wherein the signal source is a permanent magnet and the sensor is a Hall effect switch.

10. The system of claim 8, wherein the computing device includes a display and the message comprises a visual message displayed on the display of the computing device.

11. The system of claim 8, wherein the computing device is further configured initiate a communication with the orthopaedic care provider in response to the cycle count exceeding the reference threshold value.

12. The system of claim 11, wherein the computing device is configured to generate an e-mail to the orthopaedic care provider.

13. The system of claim 11, wherein the computing device is configured to initiate a telephone call to an office of the orthopaedic care provider.

14. The system of claim 11, wherein the computing device comprises:
   communication circuitry;
   a display;
   a processor; and
   memory having stored therein a plurality of instructions that, in response to the processor, cause the processor to:
   generate a visual message to the patient to the patient on the display that indicates a need to initiate communication with the orthopaedic care provider in response to the cycle count exceeding the reference threshold value, and
   initiate a communication with the orthopaedic care provider in response to the cycle count exceeding the reference threshold value.

* * * * *